US012440366B2

(12) United States Patent
Park

(10) Patent No.: US 12,440,366 B2
(45) Date of Patent: Oct. 14, 2025

(54) HUMAN BODY FLEXION AND EXTENSION ASSIST DEVICE

(71) Applicant: Donggwan Park, Busan (KR)

(72) Inventor: Donggwan Park, Busan (KR)

( * ) Notice: Subject to any disclaimer, the term of this patent is extended or adjusted under 35 U.S.C. 154(b) by 779 days.

(21) Appl. No.: 17/728,678

(22) Filed: Apr. 25, 2022

(65) Prior Publication Data

US 2022/0409418 A1 Dec. 29, 2022

(30) Foreign Application Priority Data

Jun. 25, 2021 (KR) ........................ 10-2021-0083193

(51) Int. Cl.
*A61F 5/02* (2006.01)
*A61H 1/02* (2006.01)
*A61F 5/01* (2006.01)

(52) U.S. Cl.
CPC ............... *A61F 5/028* (2013.01); *A61H 1/02* (2013.01); *A61F 2005/0179* (2013.01)

(58) Field of Classification Search
CPC .......... A61H 1/00; A61H 1/02; A61H 1/0237; A61H 1/0274; A61H 1/0292; A61H 2203/04; A61H 2203/0406; A61H 2203/0425; A61H 2205/00; A61H 2205/08; A61H 2205/081; A61H 2205/083; A61H 2205/084; A61H 2230/62; A61H 2230/625; A61H 2201/12; A61H 2201/1238; A61H 2201/1246; A61H 2201/1269; A61H 2201/1619; A61H 2201/1623; A61H 2201/1676; A61F 5/00; A61F 5/02; A61F 5/026; A61F 5/028; A61F 5/01; A61F 2005/0179; A61F 2/50; A61F 2002/5007; A61F 2002/5016; A61F 2002/5018; A61F 2002/5038; A61F 2002/5039; A61F 2002/5043
USPC .................................... 601/5; 623/27, 30, 57
See application file for complete search history.

(56) References Cited

U.S. PATENT DOCUMENTS 903,403 A * 11/1908 Quick ..................... A61F 5/028 602/20
4,829,989 A * 5/1989 Deamer ........... A63B 21/00181 602/19
5,282,460 A * 2/1994 Boldt ....................... B25J 9/146 403/119

(Continued)

FOREIGN PATENT DOCUMENTS

JP 2015-6266 A 1/2015
JP 2017-131971 A 8/2017

(Continued)

*Primary Examiner* — Colin W Stuart

(57) ABSTRACT

Provided is a human body flexion and extension assist device that is in close contact with a back, a pelvis, and a thigh of the human body to exert an assisting force to a flexion and extension motion of an upper body. According to a human body flexion and extension assist device according to the present disclosure, it is possible to store energy by a lower back flexing motion, and conversely, assist the human body by transmitting energy to a lower back extending motion. In addition, it is possible to determine a current motion of a human body, determine when an assisting force is delivered to a lower body, and minimizing discomfort by moving a lower body freely when assisting force is unnecessary.

9 Claims, 11 Drawing Sheets

(56) References Cited

U.S. PATENT DOCUMENTS

| | | | | |
|---|---|---|---|---|
| 5,876,361 | A * | 3/1999 | Harris | A61F 5/024 602/19 |
| 7,833,182 | B2 * | 11/2010 | Hughes | A61F 5/026 602/5 |
| 8,057,410 | B2 * | 11/2011 | Angold | A61H 3/008 601/5 |
| 8,801,641 | B2 * | 8/2014 | Kazerooni | A61H 1/0244 601/5 |
| 9,808,073 | B1 * | 11/2017 | Maxwell | A61H 3/008 |
| 10,278,885 | B1 * | 5/2019 | Smith | A61H 3/00 |
| 12,029,674 | B2 * | 7/2024 | Kazerooni | A61F 5/02 |
| 2009/0292369 | A1 * | 11/2009 | Kazerooni | A61H 3/00 128/845 |
| 2010/0094185 | A1 * | 4/2010 | Amundson | A61F 5/0102 623/27 |
| 2020/0171648 | A1 * | 6/2020 | Tung | A61H 1/0244 |
| 2021/0007874 | A1 | 1/2021 | Galiana Bujanda et al. | |
| 2021/0113412 | A1 * | 4/2021 | Holgate | A61H 1/0255 |
| 2022/0142803 | A1 * | 5/2022 | Ochoa | A61F 5/026 |

FOREIGN PATENT DOCUMENTS

| | | | | |
|---|---|---|---|---|
| JP | 6197160 | B1 | 9/2017 | |
| JP | 6241863 | B2 | 12/2017 | |
| JP | 2018-061663 | A | 4/2018 | |
| JP | 2019-051280 | A | 4/2019 | |
| KR | 10-2157514 | B1 | 9/2020 | |
| WO | WO-2018105430 | A1 * | 6/2018 | A61F 2/54 |

* cited by examiner

HUMAN BODY FLEXION AND EXTENSION ASSIST DEVICE

CROSS-REFERENCE TO RELATED APPLICATIONS

Pursuant to 35 U.S.C. § 119 (a), this application claims the benefit of Korean Patent Application No. 10-2021-0083193, filed on Jun. 25, 2021, the contents of which are all hereby incorporated by reference herein in their entirety.

BACKGROUND OF THE DISCLOSURE

Field of the Disclosure

The present disclosure relates to a human body flexion and extension assist device, and more particularly, to an assist device that assists a flexion and extension motion by storing energy generated by a lower back flexing motion while being worn on a human body and, conversely, by exerting energy in a lower back extending motion.

Related Art

Main motions of a lower back and a pelvis in daily life are flexing forward or extending the lower back. As a representative example of such a flexion and extension motion of the human body, there are motions of sitting, standing, or lifting a weight.

The flexion and extension motion of the human body is a motion that occurs frequently in daily life, and the need to protect a lower back is high as it greatly affects the quality of life if the lower back is injured. In addition, when muscles and joints are injured or weakened, it is necessary to assist these muscles and joints to minimize discomfort in daily life.

Japanese Patent No. 6241863 discloses a human body flexion and extension assist device. However, the prior art has a problem in that it is not possible to actively determine whether to support, and thus provides an assisting force until unnecessary.

RELATED ART DOCUMENT

Patent Document

Japanese Patent No. 6241863

SUMMARY OF THE DISCLOSURE

The present disclosure solves the problems of the conventional human body flexion assist device, and provides a human body flexion and extension assist device capable of actively determining whether to assist a lower back motion.

In an aspect, a human body flexion and extension assist device includes: a leaf spring of which at least a part is curved so that the leaf spring is closely attached to a back of the human body; an upper body belt provided on one side of the leaf spring and configured to be worn on an upper body of the human body; a central frame extending to a predetermined length in both directions from a lower side of the leaf spring to support a pelvis of the human body; a gas spring having both ends connected to a rear of the leaf spring and a rear of the central frame; a pair of lower limb frames extending to a predetermined length and rotatably connected to each other about axes in a left-right direction on both sides of the central frame; lower limb belts provided on each lower side of the pair of lower limb frames and configured to be fixed to legs; and a gearbox configured to selectively limit the rotation of the lower frame.

The human body flexion and extension assist device may further include: an inclination sensor configured to detect an inclination of an upper body; a load sensor provided on a surface of the lower limb frame in close contact with the leg and configured to measure pressure; and a control unit controlling an expansion and contraction of the gas spring to limit the rotation in the gearbox when it is determined that a load is applied to the upper body based on signals measured from the inclination sensor and the load sensor.

The gearbox may be configured to include a ratchet gear and pawl, and include a driving unit configured to adjust a position of the pawl.

The control unit may control the driving unit so that the pawl constrains the ratchet gear when it is determined that the load is applied.

The control unit may control the driving unit so that the pawl does not constrain the ratchet gear when it is determined that the load is not applied.

The control unit may determine that the load is not applied based on information on the load and inclination applied when the human body walks or sits.

The human body flexion and extension assist device may further include: a first bracket extending rearward and downwardly on a rear surface of the leaf spring; and a second bracket extending from the center frame toward the rear and upper side, in which both end portions of the gas spring are rotatably connected to the first bracket and the second bracket.

The leaf spring may be constituted by an elastic member configured to be deformable according to the angle of the upper body.

The upper body belt may include: a pair of shoulder belts configured to be worn on a shoulder; and a chest belt configured to be worn on a chest.

As the upper body of the human body is flexed, the leaf spring may be bent, and the gas spring may extend, and when the upper body of the human body is erected, may be configured to apply a restoring force of the leaf spring and the gas spring acts to tow the shoulder belt and the chest belt.

DESCRIPTION OF EXEMPLARY EMBODIMENTS

Figure 1:
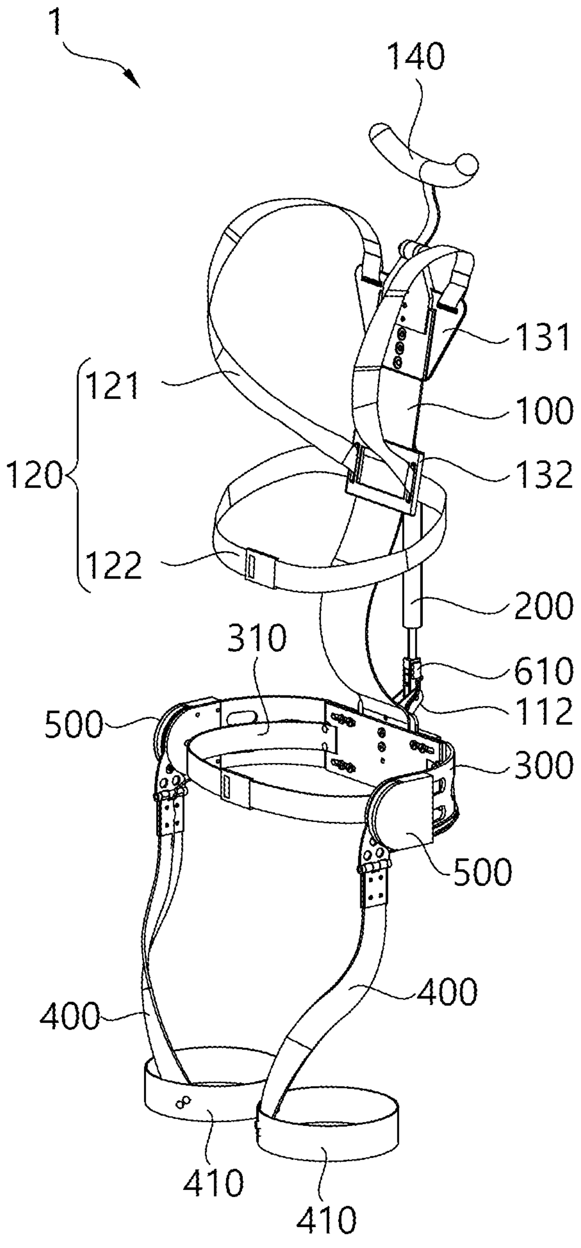
FIG. 1 is a perspective view of a human body flexion and extension assist device according to an embodiment of the present disclosure.

Hereinafter, a human body flexion and extension assist device according to an embodiment of the present disclosure will be described in detail with reference to the accompanying drawings. In the description of the embodiments below, names of each component may be referred to as another name in the art. However, if these components have functional similarity or are identical, even if a modified embodiment is employed, they may be regarded as having an equivalent configuration. In addition, reference numerals added to each component are described for convenience of description. However, the contents shown in the drawings in which these reference numerals are written do not limit each component to the scope within the drawings. Similarly, even if an embodiment in which the configuration in the drawings is partially modified is employed, if these components have functional similarity and sameness, they may be regarded as having an equivalent configuration. In addition, if a person skilled in the art recognizes that these components are components to be included, a description thereof will be omitted.

Figure 2:
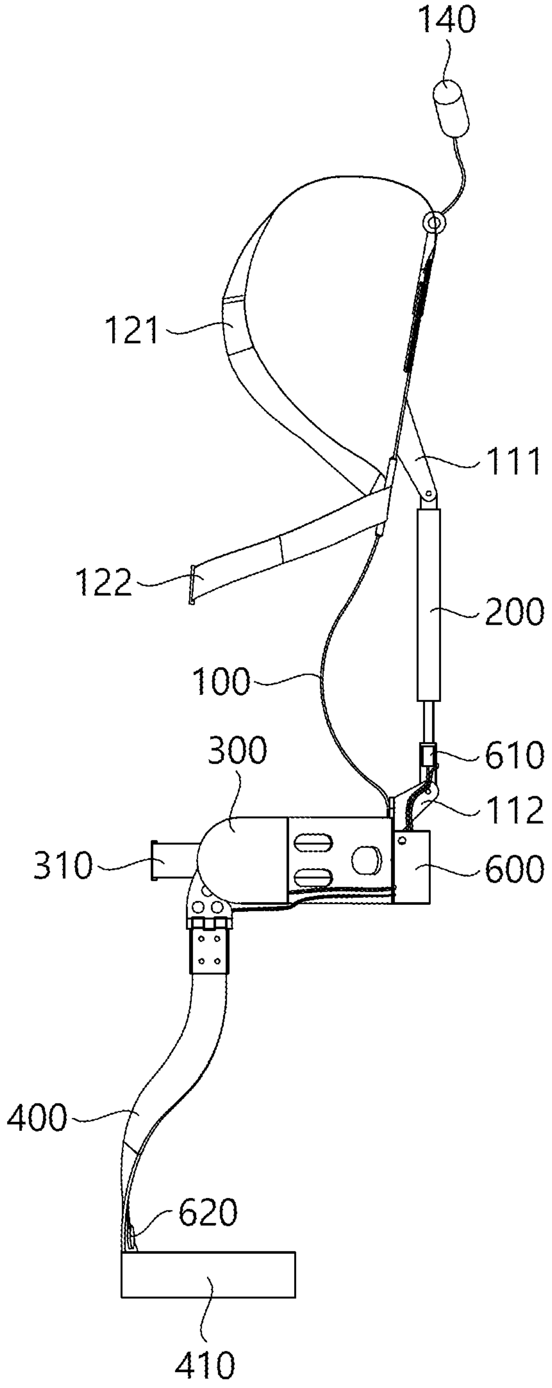
FIG. 2 is a side view of the human body flexion and extension assist device according to the embodiment of the present disclosure.
Figure 3:
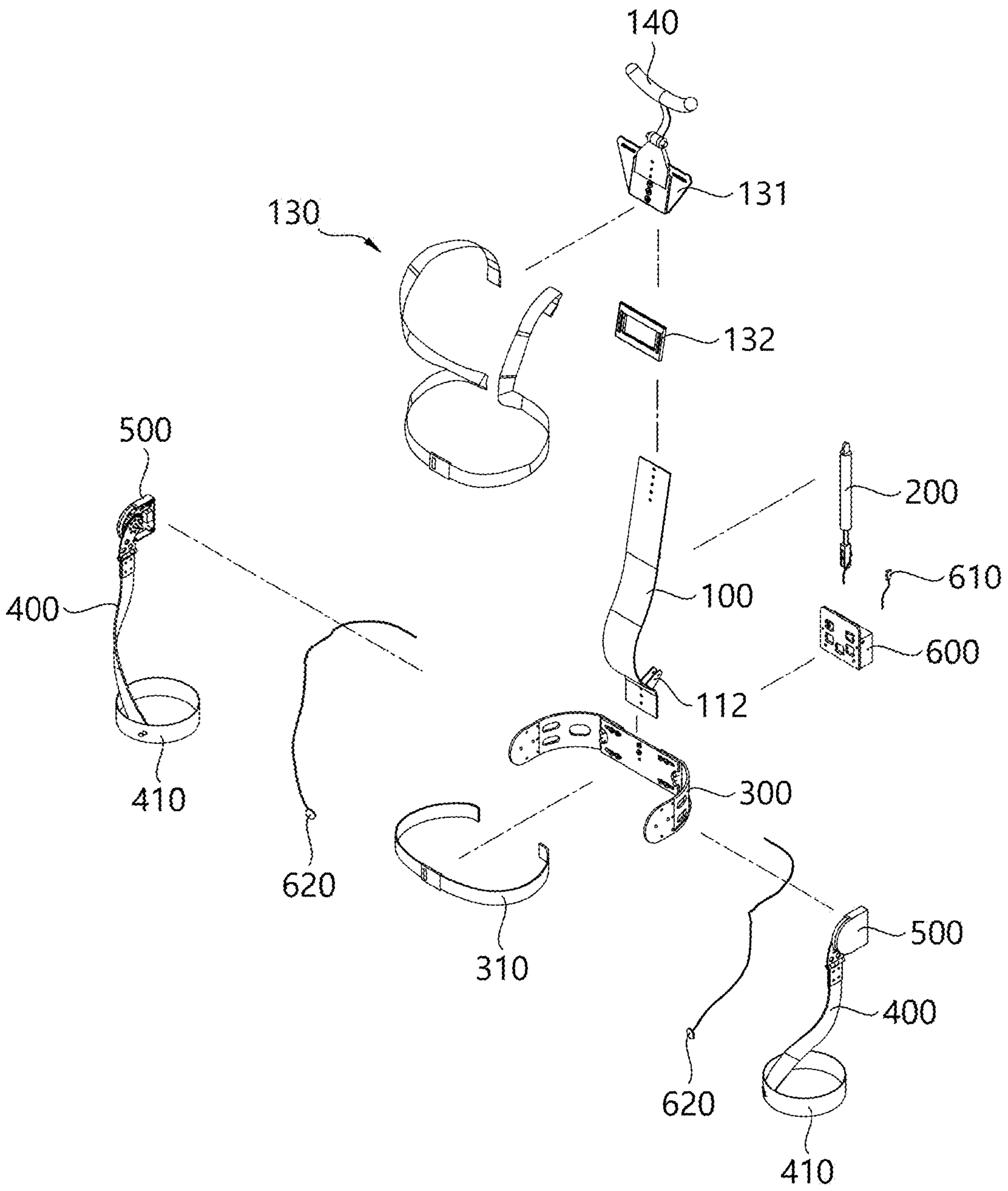
FIG. 3 is an exploded perspective view of the human body flexion and extension assist device according to the embodiment of the present disclosure.

FIG. 1 is a perspective view of a human body flexion and extension assist device according to an embodiment of the present disclosure, FIG. 2 is a side view of the human body flexion and extension assist device according to the embodiment of the present disclosure, and FIG. 3 is an exploded perspective view of the human body flexion and extension assist device according to the embodiment of the present disclosure.

Referring to FIGS. 1 and 2, a human body flexion and extension assist device 1 according to the present disclosure may be configured so that one side may be worn on an upper side of the human body, and the other side may be worn on a lower limb of the human body to assist.

The human body flexion and extension assist device 1 according to the present disclosure may be configured to include a leaf spring 100, a gas spring 200, an upper body belt 120, a headrest 140, a central frame 300, a pelvic belt 310, a lower limb frame 400, a lower limb belt 410, a gearbox 500, a control unit 600, and a sensor unit.

The leaf spring 100 is configured to be in close contact with at least a portion of a back along a spine, and may be configured in a shape corresponding to an anatomical angle of the spine. For example, the leaf spring 100 may be formed by extending a lower back portion along a convex curved path toward a front side. The leaf spring 100 is formed to have a predetermined width, but may be determined to have a width that does not interfere with a twisting motion of the human body. Also, the leaf spring 100 may be determined to have a thickness that may have appropriate elasticity.

The gas spring 200 may be configured to be connected to both sides of the leaf spring 100 to store energy or transmit energy together with the leaf spring 100 according to a change in external force.

The gas spring 200 may be configured to include a housing and a piston inserted into the housing. One side of the gas spring 200 may be rotatably connected to a gas spring first bracket 111 formed by extending downwardly rearward from the leaf spring 100. The other side of the gas spring 200 may be rotatably connected to a gas spring second bracket 112 that is formed to extend rearwardly and upwardly from the central frame 300 to be described later. The gas spring 200 may be configured such that the leaf spring 100 is expanded and contracted at an original position, and may extend as the leaf spring 100 is bent. The gas spring 200 may be configured such that, when pressure is applied to gas and oil accommodated therein while a piston extends, and an external force is reduced to a set tensile force or less of the gas spring, the piston may be retracted and returned to its original position. In this case, the force by the gas spring 200 acts by using the leaf spring 100 as a support, so it is possible to provide a traction force to unfold the upper body with an appropriate force.

Meanwhile, it is advantageous in terms of convenience and stability that an assisting force (or supporting force) by the leaf spring 100 and the gas spring 200 is maintained similarly according to a bending angle. In this case, since a restoring force of the leaf spring becomes stronger according to the bending angle, it is possible to minimize a fluctuation of the restoring force according to the bending angle by adjusting a position of an action point by a contracting force of the gas spring. In the present disclosure, the first bracket and the second bracket are configured to extend toward the rear side of the gas spring 100 and in a direction in which end portions thereof are close to each other so that the gas spring is connected, thereby minimizing a difference in assisting force depending on the bending angle.

The upper body belt 120 is provided on an upper side of the leaf spring 100 and may be configured to be worn on the upper body of the human body. The upper body belt 120 may include a shoulder belt 121 and a chest belt 122. The shoulder belt 121 is configured as a pair, and a connection hub may be provided to fix the upper side of the pair of shoulder belts 121. The connection hub 131 is provided on the upper side of the leaf spring 100 and may be formed to extend to a predetermined length in the left-right direction, and one side of the pair of shoulder belts 121 may be connected to each of the left and right sides. The chest belt 122 generally has one side fixed at a midpoint of the leaf spring 100 and may be configured to be worn around the chest of the human body. Meanwhile, the above-described shoulder belt 121 and chest belt 122 may be configured to be connected as one, and may also be applied so that the length may be adjusted. In addition, one side may be fixed on a belt slide 132 whose position may be adjusted while sliding on the leaf spring 100. However, the configuration of such a belt may be modified and applied in a known and widely used method.

The headrest 140 is provided at an upper end portion of the leaf spring, and may be configured to support a head during a backward flexing motion while a user wears the human body flexion and extension assist device 1. The headrest 140 may be connected such that an angle may be adjusted about the leaf spring 100 and the axis of the left-right direction. In addition, it may be configured to adjust a vertical position of the headrest according to a difference in height.

The central frame 300 may be configured to support a rear side of a pelvis when worn. A lower side of the above-described leaf spring 100 may be fixedly installed in a central portion of the central frame 300. The central frame 300 may be configured in a C shape in which the front is open. That is, the central frame 300 may be formed to extend along a predetermined curved surface from the left and right toward the front from the rear.

The pelvic belt 310 may be provided on the front side of the left and right end portions of the central frame 300, and may be configured to fix an abdomen side when a user wears the human body flexion and extension assist device 1. The pelvic belt 310 may be configured to be coupled and connected as a pair corresponding to the left and right sides. However, the configuration of such a belt may be modified and applied in various well-known configurations.

The lower limb frame 400 may be configured to transmit a supporting force to the lower limb, that is, the thighs. The lower limb frame 400 is configured in a pair, and may be rotatably connected to the left and right sides of the center frame 300 about the axes in the left-right direction, respectively. The lower limb frame 400 is generally formed to extend downwardly from the left and right sides of the central frame 300, and may be formed to extend in a three-dimensional curved path. A part of the lower limb frame 400 may be bent along a spiral path such that at least a part thereof may be in close contact with a front side of a thigh.

The gearbox 500 is provided in a connection part of the lower limb frame 400 and the central frame 300, and may be configured to selectively adjust or constrain the angle by driving the control unit 600 to be described later. Meanwhile, the gearbox 500 will be described later with reference to FIG. 4.

The lower limb belt 410 is provided at a lower end of the lower limb frame 400 and may be configured so that a user may wear the lower limb belt 410 on the lower limb, that is, the thigh. Therefore, while a user wears and uses the human body flexion and extension assist device 1, a position where the lower limb frame 400 is worn on the thigh may be maintained.

The control unit 600 is provided on one side of the central frame 300 and may be configured to selectively constrain the motion of the lower limb frame 400 to be described later. The control unit 600 may be configured to constrain a movement direction of one side by driving a driving unit connected to the lower limb frame 400 based on a value sensed by a sensor unit to be described later. The control unit 600 may be configured to include a power supply (not illustrated) and a processor. Meanwhile, a detailed configuration of the control unit 600 will be described later.

The sensor unit may be configured to detect the motion of the human body. The sensor unit may be configured to include an inclination sensor 610 and a load sensor 620. The sensor unit may measure the angle of the upper body and the amount of change in the angle and transmit them to the control unit 600. In addition, the load sensor 620 may be configured to be provided on the portion of the lower limb frame 400 in close contact with the thigh to measure the pressure. The inclination sensor 610 may be provided in various well-known configurations, such as a gyro sensor and an acceleration sensor. In addition, the load sensor 620 may be configured in various well-known configurations capable of measuring pressure or force.

Meanwhile, a wire connecting the sensor unit, the control unit 600, and the driving unit may be provided. At least a portion of the wiring may be disposed along the lower limb frame 400 or the central frame 300.

Hereinafter, the gearbox 500 will be described in detail with reference to FIG. 4.

Figure 4:
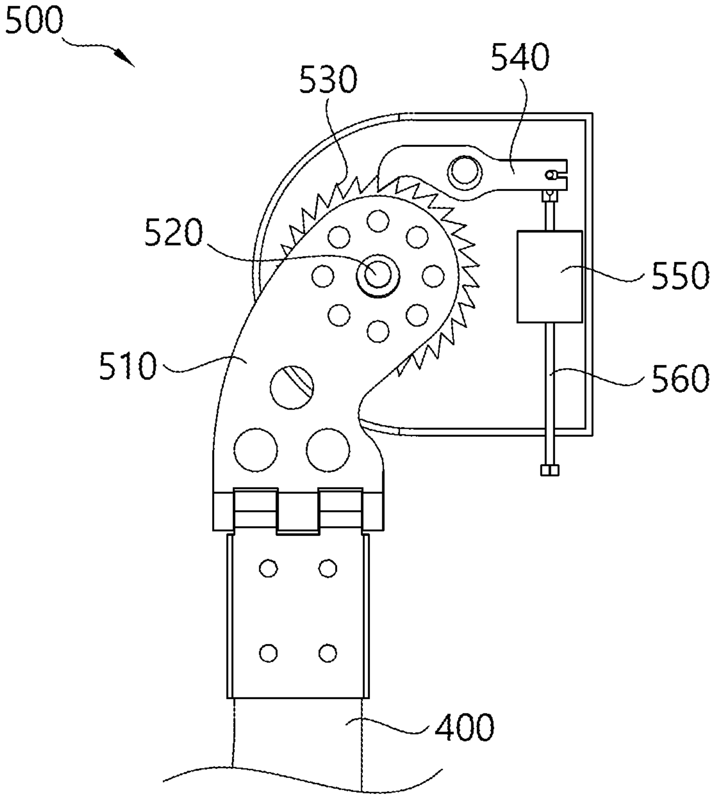
FIG. 4 is a partially cut-away view of a gearbox.

FIG. 4 is a partially cut-away view of the gearbox 500. In FIG. 4, the gearbox 500 provided on the left side of the human body flexion and extension assist device 1 when worn by a user will be described, but the gearbox 500 may be provided symmetrically on the right side as well, and a description thereof will be omitted.

Referring to FIG. 4, the gearbox 500 may be provided at a connection part between the lower limb frame 400 and the central frame 300. The gearbox 500 may be configured to include a ratchet gear skirt 510, a ratchet gear shaft 520, a ratchet gear, a pawl 540, a driving unit, and a manual control knob 560.

The ratchet gear skirt 510 may be configured to be connected to the ratchet gear 530 and to rotate together. The ratchet gear skirt 510 is formed to extend to a predetermined length, an upper side thereof may be connected to the ratchet gear 530, and a lower side may be rotatably connected to the lower limb frame 400. A hinge may be rotatably provided between the ratchet gear skirt 510 and the lower limb frame 400. The hinge may be configured such that the lower limb frame 400 is relatively rotatably connected with the ratchet gear skirt 510 about the axis in the front-rear direction. Therefore, when a user widens or narrows the lower limbs in the left-right direction, the angle in the left-right direction of the lower limb frame 400 may be adjusted naturally without resistance. On the other hand, the supporting force in the vertical direction may be transmitted through the ratchet gear skirt 510.

The ratchet gear shaft 520 is configured such that the ratchet gear 530 may rotate about an axis in a left-right direction on the central shaft. The ratchet gear 530 may have a predetermined length and may be rotatably connected to at least one of the ratchet gear 530 and the main shaft.

The ratchet gear may be configured to have a predetermined outer diameter, and may be configured to work with the pawl 540 to allow rotation in one direction, but to constrain the other direction. An allowable direction of the ratchet gear 530 may be determined as a direction in which a user moves the thigh rearward when a user wears the human body flexion and extension assist device 1. Conversely, the direction of moving the thigh forward is constrained by the pawl 540 so that the ratchet gear 530 may be configured not to rotate. In this case, when the lower body is fixed, the motion in the direction in which the lower back is flexed is constrained, and the motion in the direction in which the lower back extends is made freely.

The pawl 540 may be configured to act with the above-described ratchet gear 530 to determine the rotational direction of the ratchet gear 530. The pawl 540 may be rotatably connected to a point on the gearbox 500. One side of the pawl 540 is connected to a bidirectional solenoid 550 to be described later, so that an action of engaging with the ratchet gear 530 may be made or released. That is, when the angle of the pawl 540 is adjusted and the ratchet gear 530 is not in contact with the ratchet gear 530, the ratchet gear 530 may rotate freely, and when the angle of the pawl 540 is adjusted to contact the ratchet gear 530, as described above, the lower limb frame 400 is rotatable only in one direction.

The driving unit may be configured to be adjusted to two positions by a control input of the control unit 600. The driving unit may be configured as, for example, a bidirectional solenoid 550. The bidirectional solenoid 550 is connected to one side of the pawl 540 to selectively adjust the position of the pawl 540 by an external control input. Therefore, the action with the ratchet gear 530 may be made or released. The bidirectional solenoid 550 may have a plunger provided therein and may be moved in an operating direction. One side of the plunger is formed to extend in the operating direction, and may be rotatably connected to one side of the pawl 540.

The manual control knob 560 may be connected to the other side of the above-described plunger. The manual control knob 560 may be configured to extend to a predetermined length to be exposed to the outside of the gearbox 500. A user may adjust the position of the pawl 540 by selectively pulling or pushing the manual control knob 560 even when there is no separate control input. That is, it is possible to manually constrain or release the rotation direction of the ratchet gear 530.

Hereinafter, an operation when providing the assisting force in the human body flexion and extension assist device 1 according to the present disclosure will be described with reference to FIGS. 5A and 5B. For convenience of explanation, only the leaf spring 100 and the gas spring 200 are shown in a side view, and the remaining components are omitted.

Figure 5A:
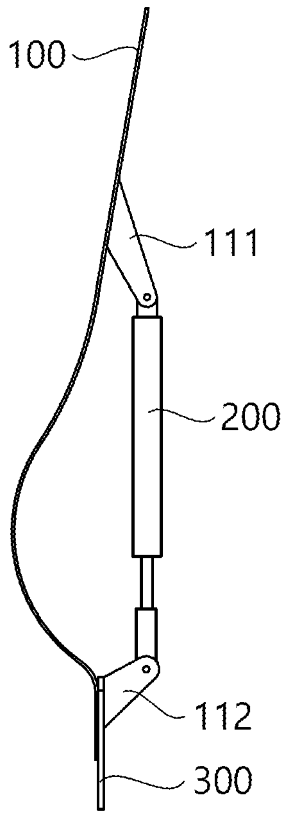
FIGS. 5A and 5B are diagrams of an operation state of a leaf spring and a gas spring.
Figure 5B:
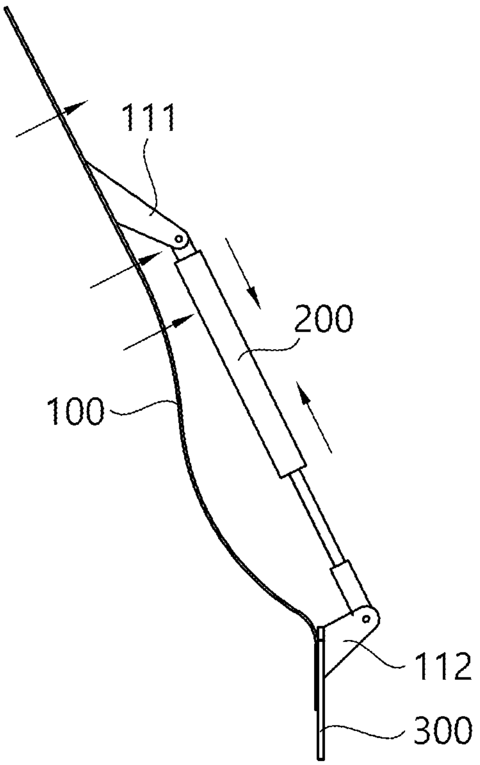

FIGS. 5A and 5B are operational state diagrams of the leaf spring 100 and the gas spring 200.

Referring to FIG. 5A, an initial state is illustrated when no external force is applied. In this case, the leaf spring 100 may be configured to be appropriately attached to the flexion of the back of the upper body.

Referring to FIG. 5B, when a user flexes the upper body when the central frame 300 is fixed, the leaf spring 100 is bent forward along the upper body, and the gas spring 200 also stores energy while extending to store energy. In this case, the leaf spring 100 transmits the supporting force to the back while being appropriately deformed in response to the flexion of the upper body. The leaf spring 100 and the gas spring 200 provide the restoring force for restoring the stored energy to the state of FIG. 5A. The leaf spring 100 provides the restoring force by its elasticity, and the gas spring 200 transmits the restoring force while being expanded and contracted. In this case, the gas spring first bracket 111 and the gas spring second bracket 112 are spaced apart from the leaf spring 100 by a predetermined distance and extend toward each other to determine the point at which the force is transmitted from the gas spring 200. In addition, since the point at which the gas spring 200 is connected to the gas spring first bracket 111 and the gas spring second bracket 112 is spaced apart from the leaf spring 100 by a predetermined distance, a torque is generated in the leaf spring 100, thereby assisting a user's lower back extending motion. The restoring force generated at this time may be transmitted to the upper body through the shoulder belt 121 and the chest belt 122.

Figure 6:
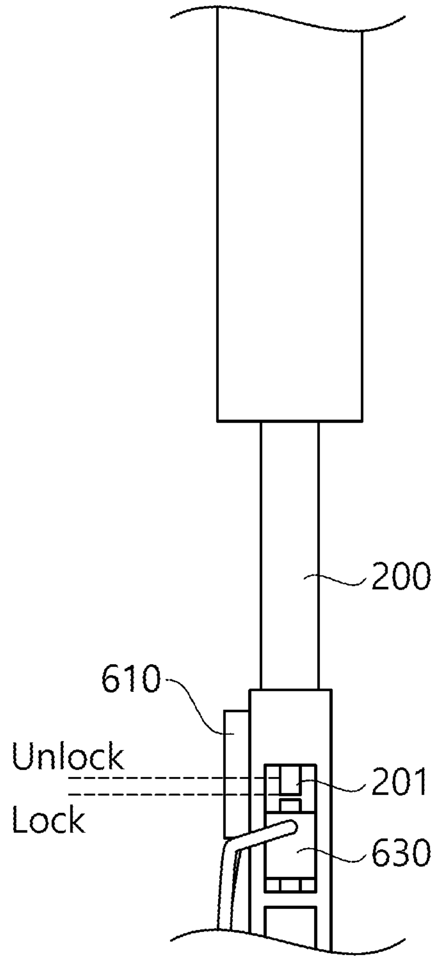
FIG. 6 is a diagram illustrating a control concept of the gas spring.

FIG. 6 is a diagram illustrating a control concept of the gas spring.

Referring to FIG. 6, the gas spring may be provided as a tension gas spring having a locking function. That is, after the gas spring extends, the gas spring may be configured to be locked by blocking a flow path when a force is applied inside the cylinder in a reverse direction. As an example, a pilot spindle 201 configured to selectively block a flow path between two chambers with the piston interposed therebetween, that is, a flow path formed on the piston, may be provided. A solenoid is provided at a lower side of the pilot spindle, and the position of the pilot spindle may be adjusted under the control of the controller. Therefore, the locking is automatically performed when the gas spring 200 extends, and then, when the gas spring 200 is returned to its original position, the control unit operates the solenoid to push the pilot spindle 201 to unlock the gas spring. Accordingly, it is possible to actively determine the time of application of the tensile force by the gas spring according to the determination of the controller. In this case, when a user flexes the lower back, the gas spring 200 does not immediately apply the supporting force that may extend the lower back, and when it is determined that the control unit performs the operation for a user to extend the lower back, the tensile force stored in the gas spring 200 is exerted, so that it is possible to transmit the force that assists to extend the lower back.

Figure 7:
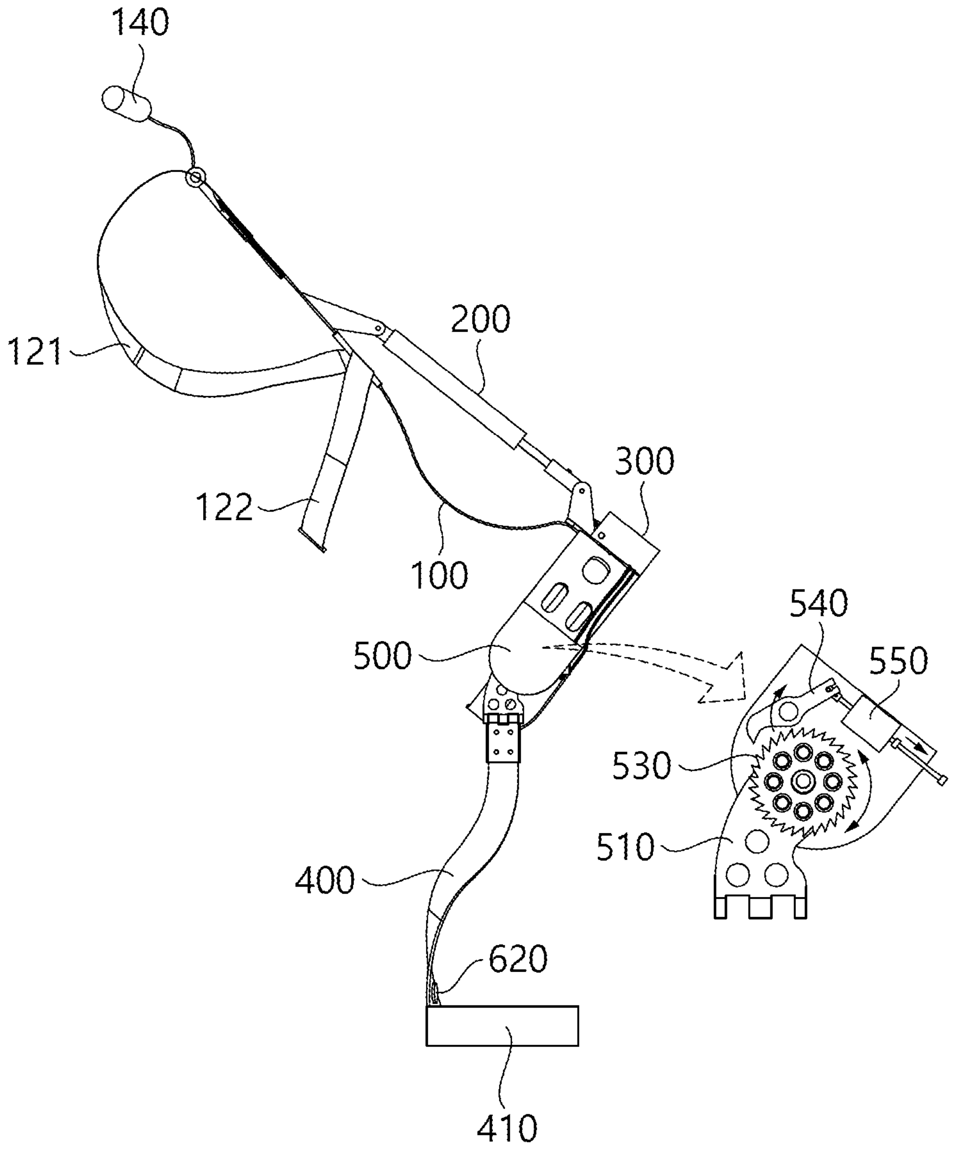
FIG. 7 is an operation state diagram when a lower frame is free to rotate.
Figure 8:
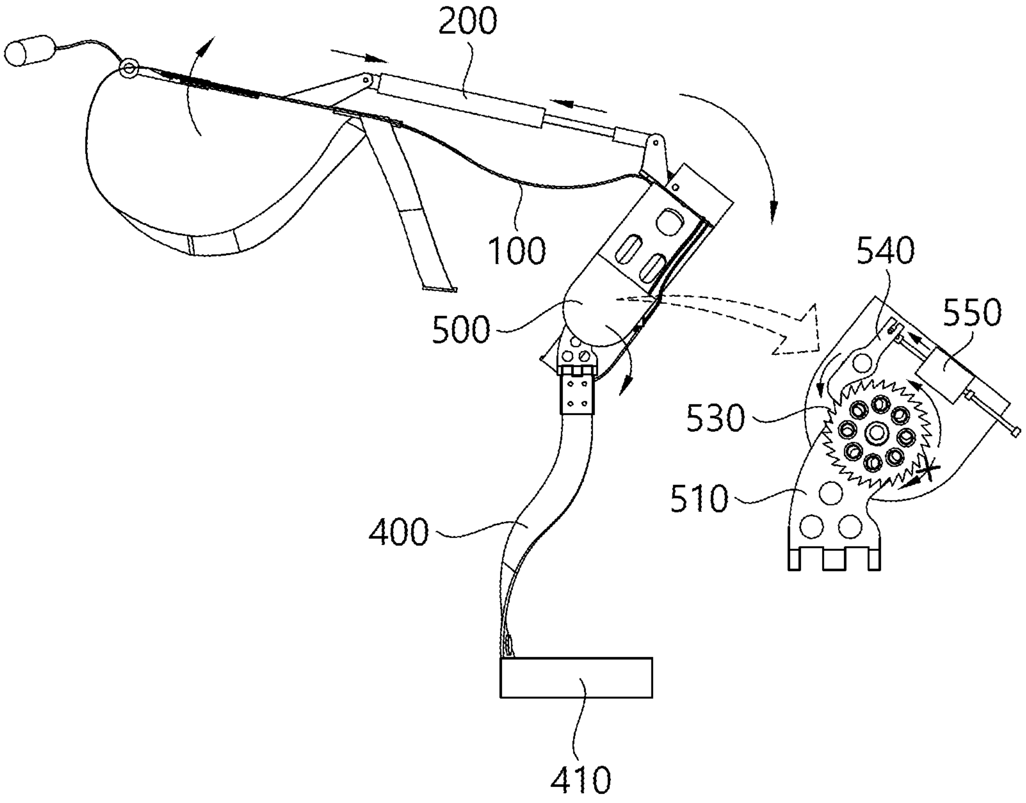
FIG. 8 is an operation state diagram when an angle of the lower frame is constrained.

Hereinafter, the operations of the control unit 600 and the lower limb frame 400 will be described in detail with reference to FIGS. 7 and 8. In FIGS. 7 and 8, description will be made on the assumption that the angle of the leaf spring 100 is adjusted when the position of the lower limb frame 400 is fixed. In addition, a partially enlarged view illustrating an internal state of the gearbox 500 in the state illustrated in FIGS. 7 and 8 is also illustrated.

FIG. 7 is an operation state diagram when the lower limb frame 400 is free to rotate, and FIG. 8 is an operation state diagram when the angle of the lower limb frame 400 is constrained.

Referring to FIG. 7, an operation state when a user sits on a structure such as a chair is illustrated. When a user sits on a chair, a sitting posture, that is, an operation in which the lower limb is flexed forward at a certain angle from the upper body, needs to be made, and in this case, a large supporting force is not required. Therefore, the control unit 600 operates the solenoid 550 to release the connection between the pawl 540 and the ratchet gear 530, and controls the lower limb frame 400 to be freely rotatable from the central frame 300. Meanwhile, the control unit 600 may receive the values of the inclination sensor 610 and the load sensor 620 and determine whether a current user is in a sitting posture, a standing up posture, or a posture lifting a weight. As an example, the control unit 600 may determine a sitting process when the value of the load sensor 620 is less than or equal to a predetermined value, the inclination of the upper body is bent at a predetermined angle, and is about to be lowered. Therefore, in this case, the rotation of the lower limb frame 400 is freely controlled.

Referring to FIG. 8, the control unit 600 determines whether a user is a standing up motion and a weight lifting motion based on the measured values of the inclination sensor 610 and the load sensor 620, and constrains the rotation angle of the ratchet gear 530 so that the supporting force may be transmitted. The control unit 600 actuates the solenoid 550 for transmission of the supporting force and engages the pawl 540 with the ratchet gear 530. Therefore, the restoring force for extending the upper body, that is, the restoring force exerted by the leaf spring 100 and the gas spring 200 is applied in the direction of extending the leaf spring 100 based on the lower limb frame 400 and the central frame 300. In this case, the restoring force applied to user is simultaneously supported and exerted by the central frame 300 in close contact with the pelvic side and the lower limb frame 400 in close contact with the lower limb. Therefore, it is possible to disperse the supporting force and implement the stable supporting.

Meanwhile, the control unit 600 controls the solenoid 550 based on the case where the angle of the inclination sensor 610 is a value generated by a typical standing up motion such as flexing and then extending the upper body to engage the pawl 540 with the ratchet gear 530.

Hereinafter, an example of use of the human body flexion and extension assist device 1 according to the present disclosure will be described with reference to FIGS. 9 and 10.

Figure 9:
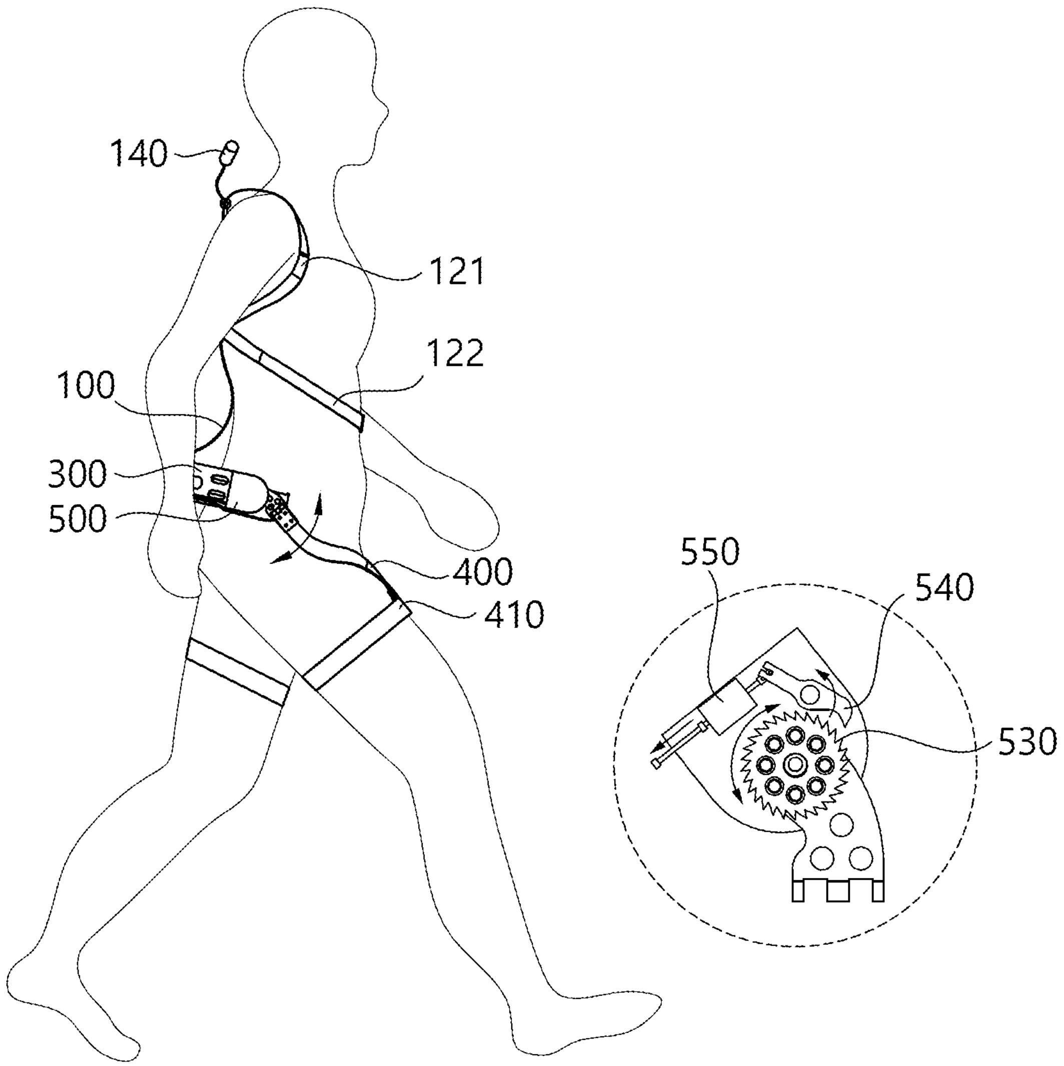
FIG. 9 is a use state diagram of the human body flexion and extension assist device according to the embodiment of the present disclosure.

FIG. 9 is a use state diagram of the human body flexion and extension assist device 1 according to the embodiment of the present disclosure.

Referring to FIG. 9, when it is determined that a user is walking, the control unit 600 may control the solenoid 550 to release the association between the pawl 540 and the ratchet gear 530. In this case, the control unit 600 determines that a user is currently walking when the value measured from the load sensor 620 is less than or equal to a predetermined value and the value of the inclination sensor 610 is greater than or equal to a predetermined value, that is, based on data measured from a typical walking motion. In this case, the rotation of the ratchet gear 530 is not constrained, so the supporting force is not transmitted by the flexing assist device 1, so a user may freely move the lower body and walk.

Figure 10:
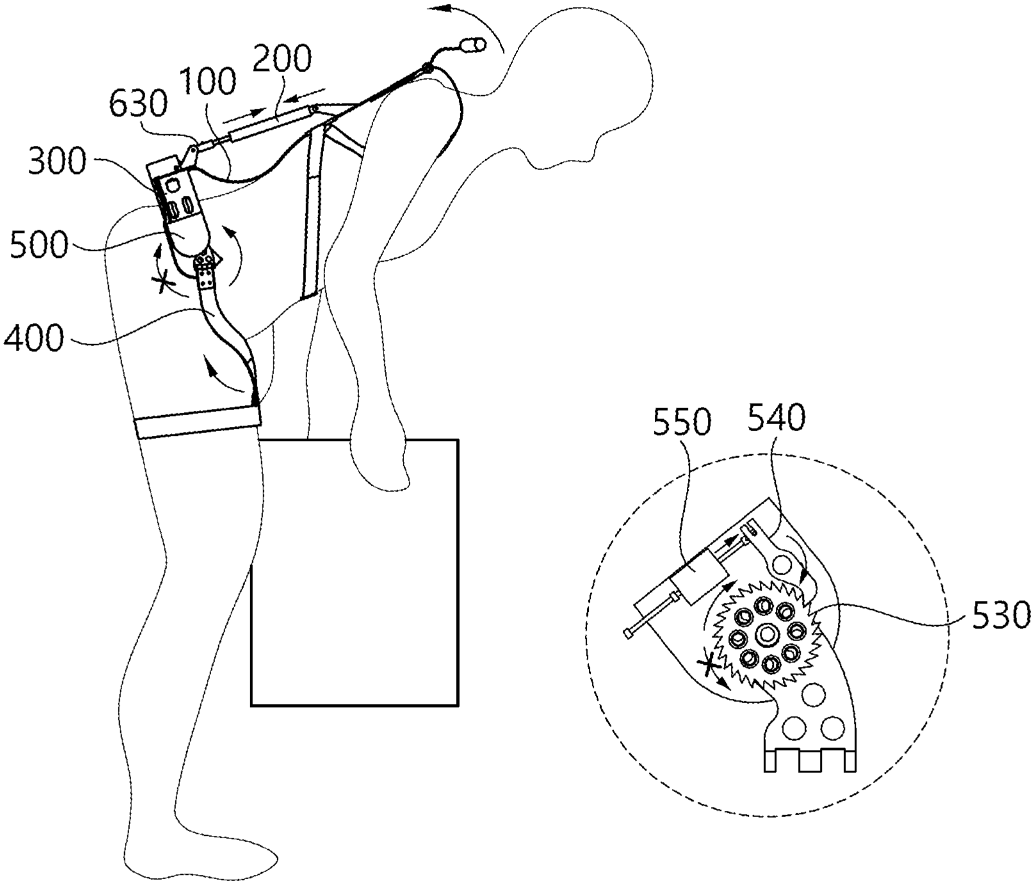
FIG. 10 is another use state diagram of the human body flexion and extension assist device according to the embodiment of the present disclosure.

FIG. 10 is another use state diagram of the human body flexion and extension assist device 1 according to the embodiment of the present disclosure.

Referring to FIG. 10, when the value measured from the inclination sensor 610 is greater than or equal to a certain value, the control unit 600 determines that a user will sit with the upper body flexed or lift a weight without walking, and operates the solenoid 550 to engage the pawl 540 with the ratchet gear 530. That is, the ratchet gear is locked so that it can rotate in only one direction. The flexing of the human body in the state in which the ratchet gear is fixed is stored as an elastic repulsive force by bending the leaf spring 100, and is stored as a tensile force by simultaneously expanding the gas spring 200. In this case, the gas spring in the expanded state may be locked. On the other hand, when lifting a weight, the load transmitted to the upper body is transmitted to the leaf spring 100 through the shoulder belt 121 and the chest belt 122, and is also transmitted to the central frame 300 and the lower limb frame 400. As a result, since the value of the load sensor 620 provided between the lower limb frame 400 and the thigh increases, the control unit 600 may determine whether or not the human body is flexed based on this.

The control unit 600 determines that it is a forward flexing motion of the human body, that is, a weight lifting motion, to operate the gas spring control solenoid 630 to release the locking of the gas spring and exert the tensile force. Therefore, the supporting force is exerted so that the user's upper body is not further flexed based on the lower body. That is, when lifting a weight, the supporting force that keeps it from lowering below the lifted height may be exerted. In the user's lower back extending motion, a user may extend the upper body by the force exerted by the user, the force that tows the upper body by the leaf spring 100 and the gas spring 200, and when the traction force by the leaf spring 100 and the gas spring 200 is removed, the pawl 540 allows the ratchet gear 530 to rotate and the movement of the lower frame becomes free.

On the other hand, in the above-described FIGS. 7 to 10, an example in which the rotation direction of the lower limb frame 400 is constrained by the control unit 600 has been described, but the user may manually constrain the rotation direction of the ratchet gear 530 by pushing or pulling the manual control knob 560 exposed to the gearbox 500.

As described above, according to the human body flexion and extension assist device according to the present disclosure, it is possible to store energy by the lower back flexing motion, and conversely, assist the human body by transmitting energy to the lower back extending motion.

In addition, it is possible to determine a current motion of a human body, determine when an assisting force is delivered to a lower body, and minimizing discomfort by moving a lower body freely when assisting force is unnecessary.

What is claimed is:

1. A human body flexion and extension assist device, comprising:

a leaf spring of which at least a part is configured to be curved so that the leaf spring is closely attached to a back of a human body;

an upper body belt provided on one side of the leaf spring and configured to be worn on an upper body of the human body;

a central frame extending to a predetermined length in both directions from a lower side of the leaf spring to support a pelvis of the human body;

a gas spring having ends connected to a rear of the leaf spring and a rear of the central frame;

a pair of lower limb frames extending to a predetermined length and rotatably connected to each other about a left-right axis on both sides of the central frame;

lower limb belts provided on each lower side of the pair of lower limb frames and configured to be fixed to legs;

a gearbox configured to selectively limit the rotation of the lower frame;

an inclination sensor configured to detect an inclination of an upper body;

load sensors respectively provided on surfaces of the pair of lower limb frames and configured to measure pressure; and a control unit configured to control an expansion and contraction of the gas spring and limit the rotation in the gearbox when it is determined that a load is applied to the upper body based on signals measured from the inclination sensor and the load sensors.

2. The human body flexion and extension assist device of claim 1, wherein the gearbox is configured to include a ratchet gear and pawl, and includes a driving unit configured to adjust a position of the pawl.

3. The human body flexion and extension assist device of claim 2, wherein the control unit controls the driving unit so that the pawl constrains the ratchet gear when it is determined that the load is applied.

4. The human body flexion and extension assist device of claim 3, wherein the control unit controls the driving unit so that the pawl does not constrain the ratchet gear when it is determined that the load is not applied.

5. The human body flexion and extension assist device of claim 4, wherein the control unit determines that the load is not applied based on information on the load and inclination applied when the human body walks or sits.

6. The human body flexion and extension assist device of claim 1, further comprising:

a first bracket extending rearward and downwardly on a rear surface of the leaf spring; and a second bracket extending from the central frame toward the rear and upper side, wherein both end portions of the gas spring are rotatably connected to the first bracket and the second bracket.

7. The human body flexion and extension assist device of claim 6, wherein the leaf spring is constituted by an elastic member configured to be deformable according to an angle of the upper body.

8. The human body flexion and extension assist device of claim 1, wherein the upper body belt includes:

a pair of shoulder belts configured to be worn on a shoulder; and a chest belt configured to be worn on a chest.

9. The human body flexion and extension assist device of claim 8, wherein as the upper body of the human body is flexed, the leaf spring is bent, and the gas spring extends, and when the upper body of the human body is erected, is configured to apply a restoring force of the leaf spring and the gas spring acts to tow the shoulder belt and the chest belt.

* * * * *